Figure 1:
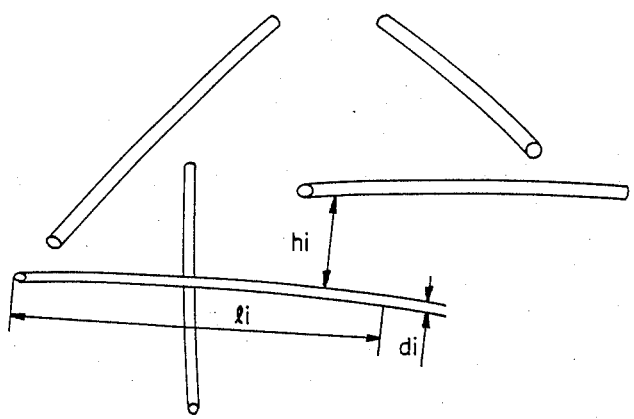

United States Patent [19]

Karaila

[11] Patent Number: 4,791,305

[45] Date of Patent: Dec. 13, 1988

[54] METHOD FOR MEASURING THE PROPERTIES OF A COMPOSITION CONSISTING OF A LIQUID AND SOLID PARTICLES AND APPARATUS USED IN THE METHOD

[75] Inventor: Ilkka Karaila, Pirkkala, Finland

[73] Assignee: Valmey Oy, Tampere, Finland

[21] Appl. No.: 271,143

[22] PCT Filed: Feb. 24, 1987

[86] PCT No.: PCT/FI87/00029
§ 371 Date: Oct. 23, 1987
§ 102(e) Date: Oct. 23, 1987

[87] PCT Pub. No.: WO87/05109
PCT Pub. Date: Aug. 27, 1987

[30] Foreign Application Priority Data

Feb. 25, 1986 [FI] Finland ............................ 860800

[51] Int. Cl.[4] .................. G01N 15/06; G01N 15/07
[52] U.S. Cl. .............................. 250/574; 356/338
[58] Field of Search .............. 250/574, 575; 356/335, 356/336, 337, 338, 339, 340, 341, 342, 343

[56] References Cited

U.S. PATENT DOCUMENTS

| 3,998,552 | 12/1976 | Stewart et al. | 356/103 |
| 4,017,186 | 4/1977 | Shofner et al. | 356/103 |
| 4,441,816 | 4/1984 | Hencken et al. | 356/335 |
| 4,449,816 | 5/1984 | Koshaka et al. | 356/338 |
| 4,714,347 | 12/1987 | Cole | 356/339 |

FOREIGN PATENT DOCUMENTS 0167272 1/1986 European Pat. Off.

Primary Examiner—David C. Nelms
Assistant Examiner—William L. Oen
Attorney, Agent, or Firm—Pollock, Vande Sande & Priddy

[57] ABSTRACT

The invention relates to a measuring method of the properties, especially the dry matter content of cellulose pulp. The most important measurement at the wet end of a paper-making machine is the measurement of dry matter content and quantity of the pulp. The material quantities can be readily measured from a finished product but the wet end optimal control requires a method and apparatus capable of measuring reliably the dry matter content of mass suspension.

18 Claims, 7 Drawing Sheets

METHOD FOR MEASURING THE PROPERTIES OF A COMPOSITION CONSISTING OF A LIQUID AND SOLID PARTICLES AND APPARATUS USED IN THE METHOD

Method for measuring the properties of a composition consisting of a liquid and solid particles and apparatus used in the method.

The present invention relates to a method as defined in the preamble of claim 1 for measuring the properties of a composition consisting of a liquid and solid particles and to an apparatus used in the method.

In particular, but not exclusively, the invention relates to a measuring method of the properties, especially the dry matter content of cellulose pulp. The most important measurement at the wet end of a paper-making machine is the measurement of dry matter content and quantity of the pulp. The material quantities can be readily measured from a finished product but the wet end optimal control requires a method and apparatus capable of measuring reliably the dry matter content of mass suspension.

Presently available are mechanical (FI 33814 and SE 343683) and optical (FI application 824185) methods and mechanisms, based on the measurement of the shearing force of a composition or the light scattered from a pulp. All these mechanisms are characterized by being non-linear and by the fact that they must be adjusted on the basis of laboratory samples. Another drawback in mechanical measuring methods are the measuring inaccuracies caused by the flow rate of a composition. A drawback in the optical composition measuring methods is that the properties of a composition, such as whiteness, chemicals, additives and variations in particle size distribution, lead to inaccuracies in the measurement. The above disturbance factors affect the outcome whenever any of them obtain a new value. In other words, the presently available mechanisms are capable of producing a signal suitable for a control operation and dependent on the dry-matter content when the dry-matter content is the only variable that changes. Variations in flow rate, composition whiteness, chemicals and additives are disturbing factors and lead to inaccuracy and adjustment requirements in the present measuring methods.

An object of this invention is to introduce a method for measuring the properties of a composition consisting of a liquid and solid particles in a manner that the method is capable of measuring the properties, especially the dry-matter content of a composition directly from the composition without allowing the other properties of a composition to affect the measuring results.

In order to achieve this object, a method of the invention is essentially characterized in that
- the electromagnetic radiation led into a composition is given a wavelength that is smaller than the smallest dimension of the particles in a composition to be measured,
- an intensity function is formed as a result of the movement of an individual particle arriving in and passing by any given zone exposed to radiation and
- the intensity function is processed for finding out time relationships that are proportional to the thus appearing properties of a particle.

Figure 2:
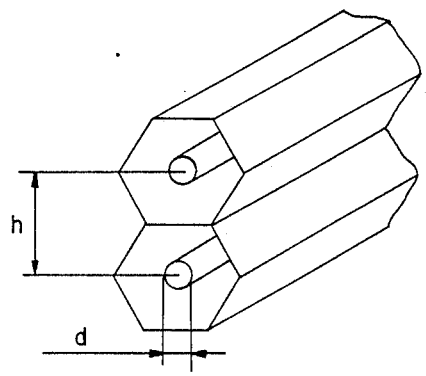

The theoretical basis of the above-described method, particularly when a composition to be measured is cellulose pulp, can be derived as follows:

Fibres in a mass suspension build a three-dimensional network on rather low consistencies. The network accumulates in so-called flocs when consistency exceeds the value of one percent. It is natural that the pulp should be as free of flocs as possible when it comes onto the wire of a paper-making machine. There are studies available indicating that such flocs are produced on consistencies over one percent in a few milliseconds when the mass is not turbulent. In other words, cellulose pulp or mass must be in continuous motion. FIG. 1 is a schematical view of cellulose pulp with cellulose fibres in random order. Thus, cellulose mass or pulp consists of disorderly bundles of fibres, in which the fibre lengths are usually in the order of 100 ... 1000 microns, sometimes more than that. The mass further contains short flour, whose length is less than 100 microns, as well as additives (clay etc.) with particle size less than 10 microns. In theory, it is conceivable that, as shown in FIG. 2, the fibres are evenly distributed over the entire mass volume. The pattern shown in FIG. 2 can be argued by pointing out that the fibres are Poisson-distributed with a certain parameter representing a relative distance h. Supposing further that the fibres have a great length l and the fibres have a certain main diameter d, it is possible to derive the dependence between mass consistency C and parameter h. It can be seen from FIG. 2 that the volume can also be divided e.g. in hexagonal elements, whose longitudinal axis coincides with the longitudinal axes of evenly distributed fibres.

The mass consistency can be described by equation $$C = m_F / V \tag{1}$$

where
$C$ = consistency g/l
$m_F$ = mass of the fibres
$V$ = volume containing the fibres on the other hand $$m_F = \rho_F V_F, \tag{2}$$

where
$\rho_F$ = fibre density (close to one)
$V_F$ = fibre volume

On the basis of the above, equations (1) and (2) lead to $$C = \rho_F V_F / V \tag{3}$$

Calculating from FIG. 2 that $$V_F = (\pi/4) d^2 \cdot l \tag{4}$$

$$V = \sqrt{3} h^2 \cdot l / 2 \tag{5}$$

Inclusion of (4) and (5) in equation (3) leads to $$C = \rho_F (\pi/4) d^2 \cdot l / (\sqrt{3} h^2 \cdot l / 2)$$

and after cancellation $$C = \pi \rho_F d^2 / (2\sqrt{3} h^2) \tag{6}$$

or $$C = \text{constant term} \cdot (d/h)^2,$$

in which a constant term $= \pi \rho_F / 2\sqrt{3}$

Equation 6 indicates that an absolute measurement of consistency is possible, provided it is possible to measure the mean fibre diameter d and the distance h between fibres, i.e. $C = f(d,h)$.

Following now is a description of the theoretical basis for the fact that such quantities d and h can indeed be measured from a fibre suspension.

Figure 3:
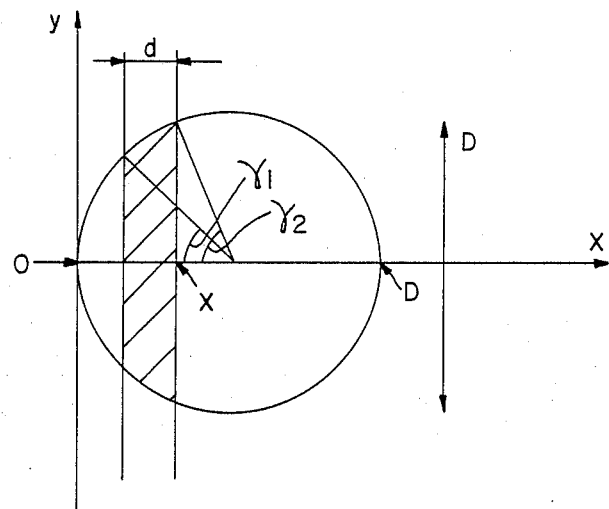

Supposing that e.g. an electromagnetic radiation is led into a mass or pulp to cover a circle whose diameter is D. Within this zone is located a d-diameter fibre, as shown in FIG. 3. As the fibre travels across the radiated zone in the direction of a positive x-axis, the shaded portion thereof will be visible. The surface area I of this portion as anti-function of the position when the fibre is within the radiated zone will be $$I_O = r^2 \cdot (\gamma_2 - \sin \gamma_2 \cos \gamma_2 - (\gamma_1 - \sin \gamma_1 \cos \gamma_1)) \quad (7)$$

where $\gamma_1$ and $\gamma_2$ are the central angles defined in the figure $I_0 = 0$, when $x < 0$ or $x > D + d$
$x = 0$, when the leading edge of a fibre touches a radiated zone
$r = D/2$
$\cos \gamma_2 = 1 - x/r$, when $C \leq x \leq D$,
$\cos \gamma_2 = 1$, when $x < 0$,
$\cos \gamma_2 = -1$, when $x > D$
$\cos \gamma_1 = \cos 2 + d/r$, when $d \leq x \leq D + d$,
$\cos \gamma_1 = 1$, when $x < d$,
$\cos \gamma_1 = -1$, when $x > D + d$ If the mass is radiated over a zone having diameter D, I will represent the intensity of reflected light as an x-function of the position of a fibre.

In digital image processing, configurations are identified by finding the sharpest-changing points in the variation of image intensity.

In order to study its variations, signal $I_0$ must be derived and the result for the first ($I_1$) and the second ($I_2$) derivative as a function of x with the designations and conditions of equation (7) will be:

$$I_1 = (dI_0/dx) = 2r \cdot (\sin \gamma_2 - \sin \gamma_1) \quad (8)$$

$$2 = (dI_1/dx) = 2 \cdot (\cot \gamma_2 - \cot \gamma_1) \quad (9)$$

Figure 4:
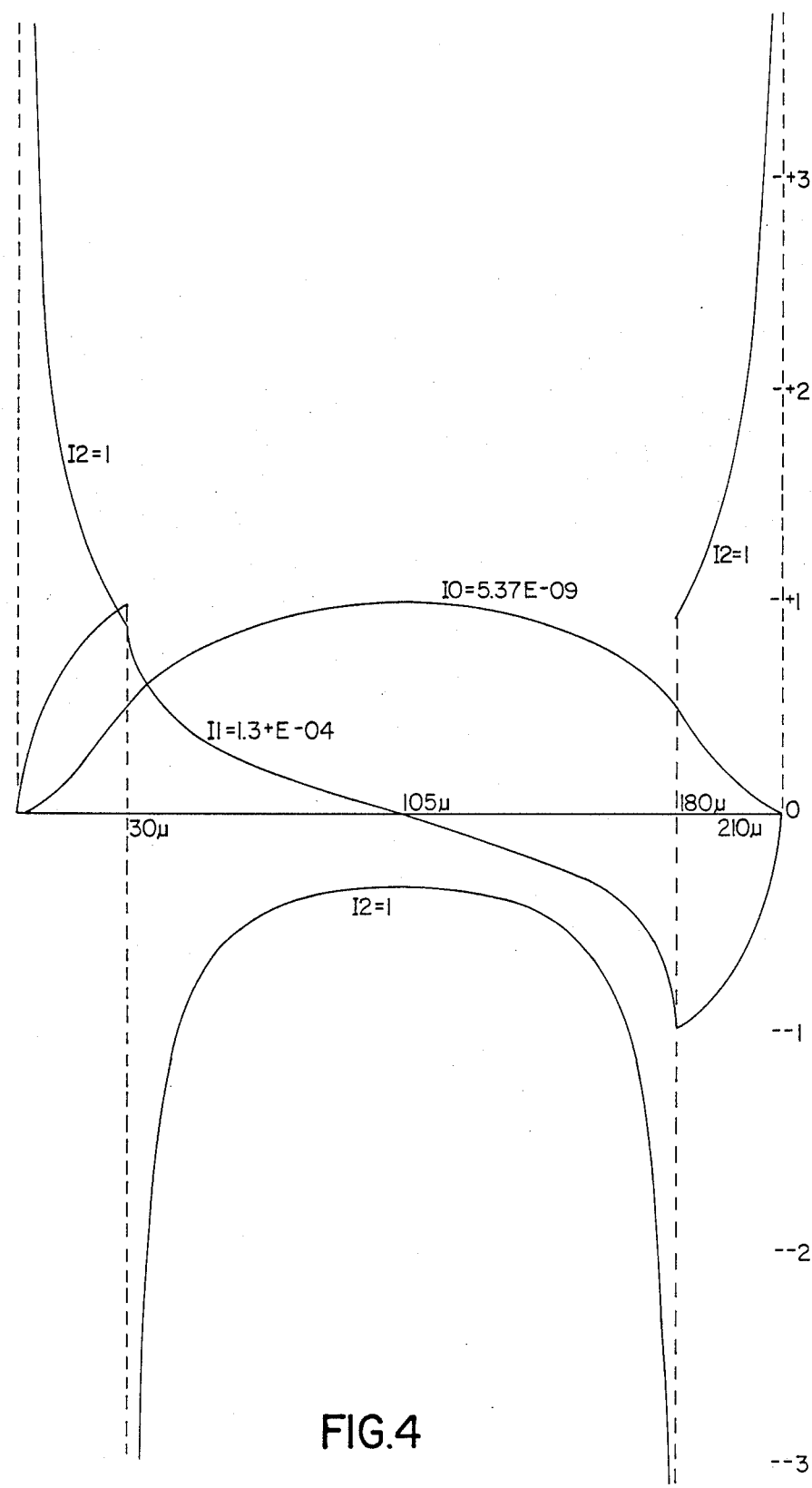

FIG. 4 shows the describers of a function $I_0$, $I_1$ and $I_2$ when the diameter of a radiated zone is 180 microns and the mean fibre diameter d is 30 microns.

The figure shows an interesting characteristic of the second derivative of function $I_0$:

$I_2$ has singularities at points $x = 0$, d, D and $D + d$.

These singularities can be derived from equation (9) by including the variables as a function of x.

Further, as a function of time, the mass travels across the examined zone at a velocity v. Since fibres are randomly positioned in the mass, the x-directed velocity obtains an average value v $$v_k = 2v/\pi \quad (10)$$

which is the average of a fibre's velocity in direction x with the position of fibres varying arbitrarily relative to the x-axis.

Intensity $I_0$ obtains a corresponding statistical coefficient $2/\pi$, since the angle between fibres and z-axis varies randomly with respect to the plane of FIG. 3.

When a suspension travels at velocity v, equations (7), (8) and (9) obtain a new form since electronics offer a possibility of deriving time functions with respect to time.

The result will be voltage functions $u_0$, $u_1$ and $u_2$:

$$u_0 = K \cdot I_0 \cdot (t) \quad (11)$$

$$u_1 = T_1 K \frac{dI_0}{dx} \frac{dx}{dt} \quad (12)$$

$$u_2 = T_1 T_2 K \frac{d^2 I_0}{dx^2} \left(\frac{dx}{dt}\right)^2 + T_1 T_2 K \frac{dI_0}{dx} \frac{d^2 x}{dt^2} \quad (13)$$

where
$K = \phi_0 \cdot \rho_0 \cdot NA_E \cdot NA_S \cdot R_\phi \cdot G$
$\phi_0$ = output emitted by a light source
$\rho_0$ = effective reflection factor of a fibre
$NA_E$ = emitter aperture
$NA_S$ = receiver aperture
$R_\phi$ = receiver sensitivity
$G$ = electronics gain
$T_1$ and $T_2$ = derivation time constants When noted that $(dx/dt) = v$, the following is observed: If a sample is obtained from voltages $u_0$ and $u_2$ when $u_1 = 0$, the last term of equation (13) can be eliminated and the ratio $u_2/u_0$ of samples is proportional to the square of flow rate.

At this point $$I_0 = r^2(\pi - 2a \tan(\sqrt{z^2 - 1} + 2z^{-1}\sqrt{1 - z^{-2}})) \quad (14)$$

$$I_2 = -4/\sqrt{z^2 - 1} \quad (15)$$

where
$r = D/2$
$z = D/d$

In addition to derivation time constants $T_1$ and $T_2$, the velocity signal obtains as a scaling factor that radius r of a radiated zone and as a disturbance term, in accordance with equations (14) and (15), a term resulting from the variations of fibre diameters.

Figure 5:
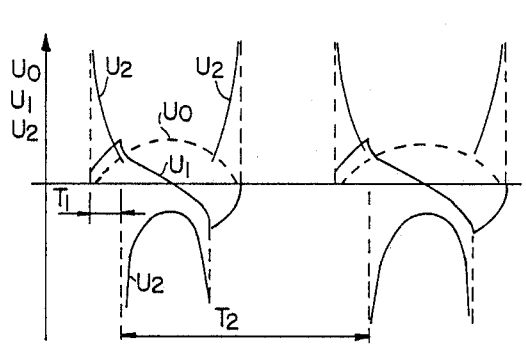

For the determination of dry matter content, according to the above formulae (formula 6), it is necessary to have information about the magnitude of d and h. FIG. 4 indicates that the interval between successive opposite-sign singularities (o, d) of $u_2$ is $T_1 = d/v$ and the repetition interval of signals is $T_2 = h/v$. The situation is outlined in FIG. 5. If a flip-flop in the electronic component of the apparatus is controlled to be on during time $T_1$ (time between singularities o—d) and off during time $T_2 - T_1$ (includes singularities D and $D + d$), a pulse sequence of FIG. 6 will be obtained. Filtration of the pulse sequence and its complement gives the voltages $$u_d = \frac{T_1}{T_2} \cdot u_s \quad (16)$$

$$u_h = \frac{T_2 - T_1}{T_2} \cdot u_s \quad (17)$$

Equation (16) can also be described as $$u_d = (d/v/n/v) \cdot u_s \quad (16a)$$

where $u_s$ = flip-flop operating voltage.

Figure 12:
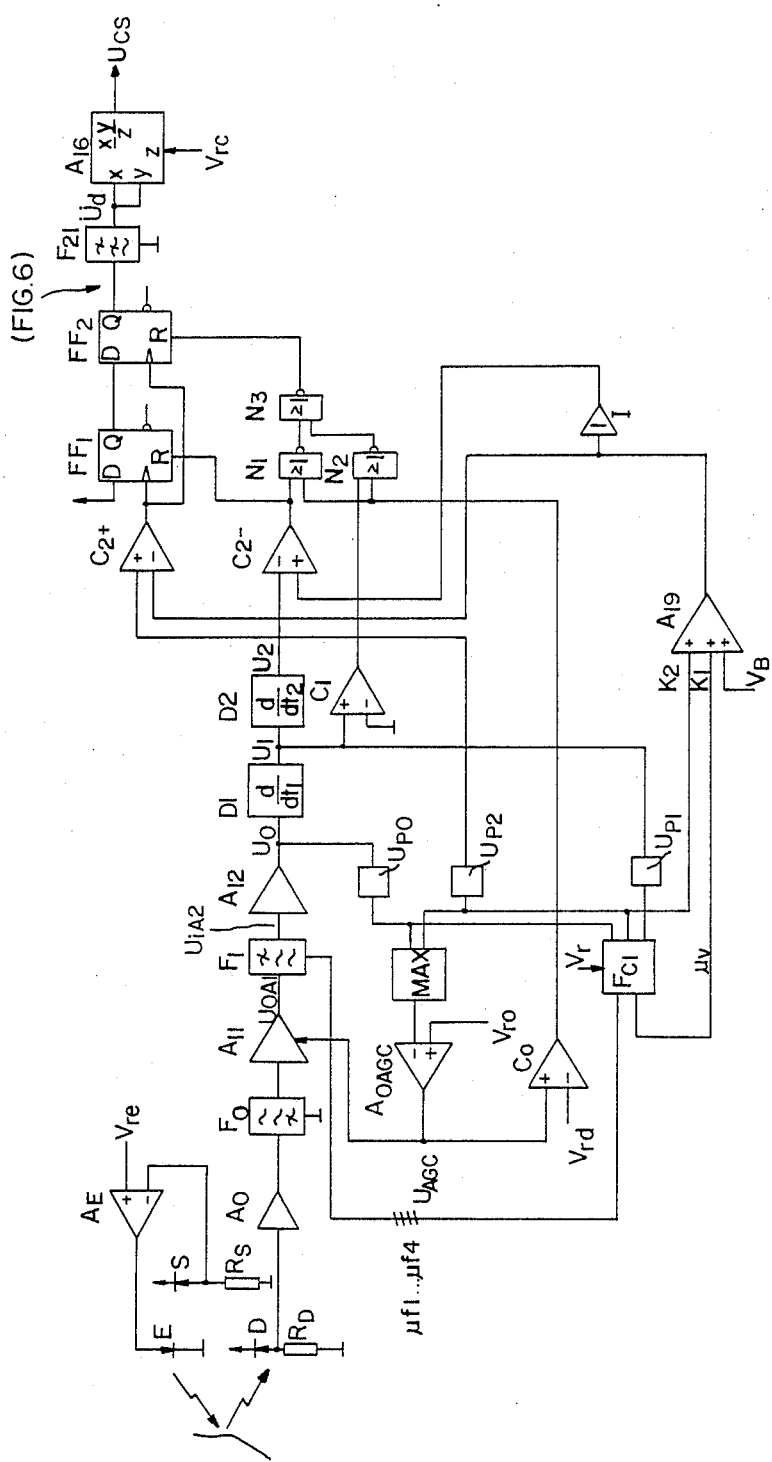

When the filtered $u_d$ is squared and scaled by dividing by voltage $V_{rc}$, the result will be a signal $u_{cs}$ proportional to consistency C of equation (6):

$$u_{cs}=(u_d{}^2/V_{rc})=(u_s{}^2/V_{rc})\cdot(d/n)2 \qquad (18)$$

where $V_{rc}$=scaling voltage for electronic circuit of FIG. 12

It can be noted that equation (18) provides a voltage equal or at least proportional to the consistency, said voltage being in principle independent of flow rate, colour and additives.

The above argument is based on the following hypotheses:
1. By means of automatic control of electronics gain factor, $u_0$ can be made constant
2. amplitude of electronics noise can be kept to such a level that the peaks of $u_2$ are distinguished with a sufficient probability
3. the mass flow rate is within suitable limits, at too low a rate, $u_2$ goes to zero and at too high a rate, the electronics passband runs out; passband must be restricted for limiting the noise to a sufficiently low level (item 2)
4. additives do not reflect light the same way as fibres, i.e. fibres must be distinguishable from background.

Thus, the above describes how the dry matter content of a composition can be measured according to the characterizing section of claim 1.

According to the method, it is hence possible to measure the dry matter content of a composition directly from the composition, whereby the measurement disturbing factors can be more readily controlled. A condition for this operation is that the particles to be measured are to such a degree distinguishable from the background that the noise in a signal derived from a signal produced by said particles and due to a detector and electronics does not override said utility signal. Other features characteristic of the method as well as the apparatus are set forth in the other annexed claims. As for the advantages gained thereby, reference is made to the above section explaining the theoretical basis of the invention.

Figure 13:
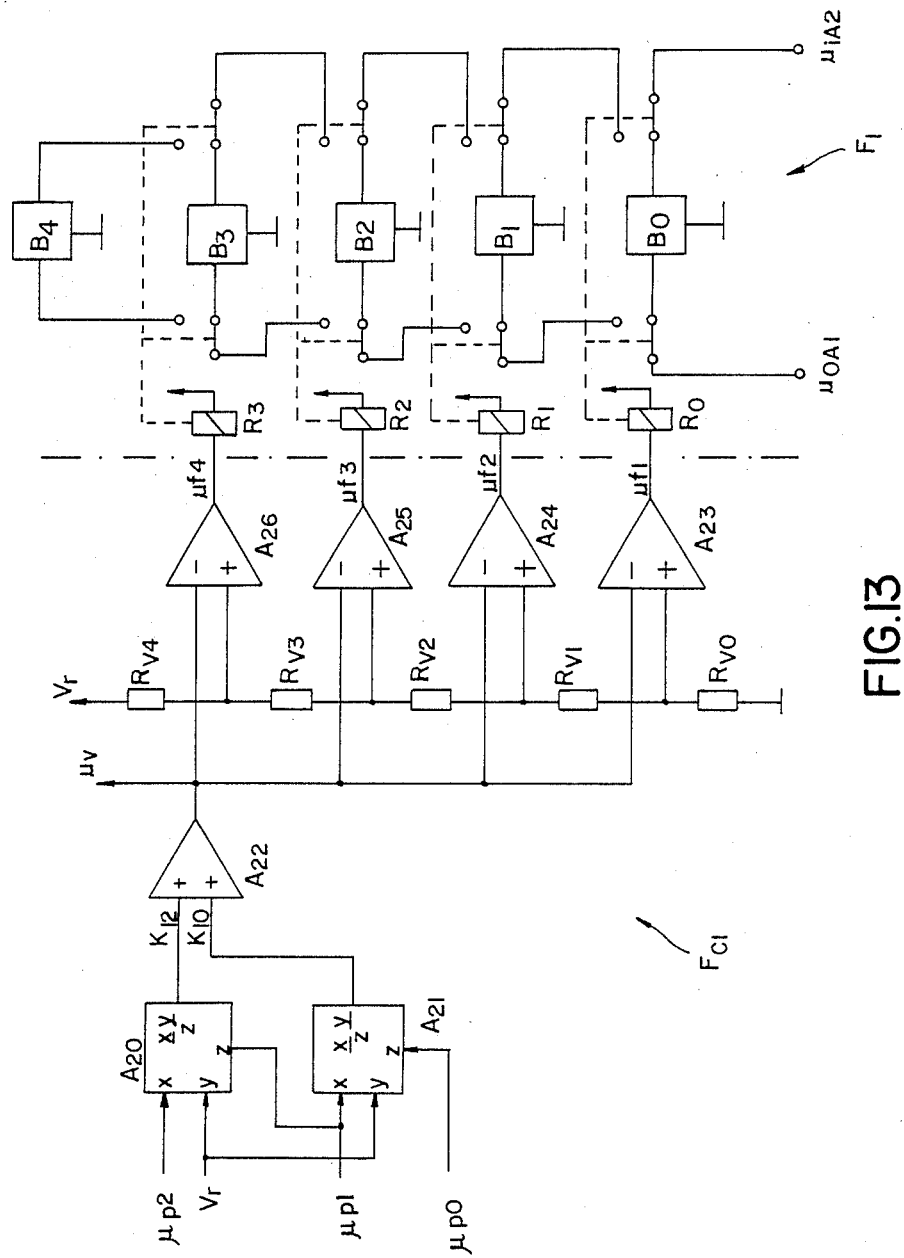

Alternative embodiments of an apparatus of the invention are schematically illustrates in FIGS. 7–11 and one preferred diagram for the electronics component of said apparatus is shown in FIGS. 12 and 13. The apparatus will now be described in more detail with reference made to those figures.

Figure 7:
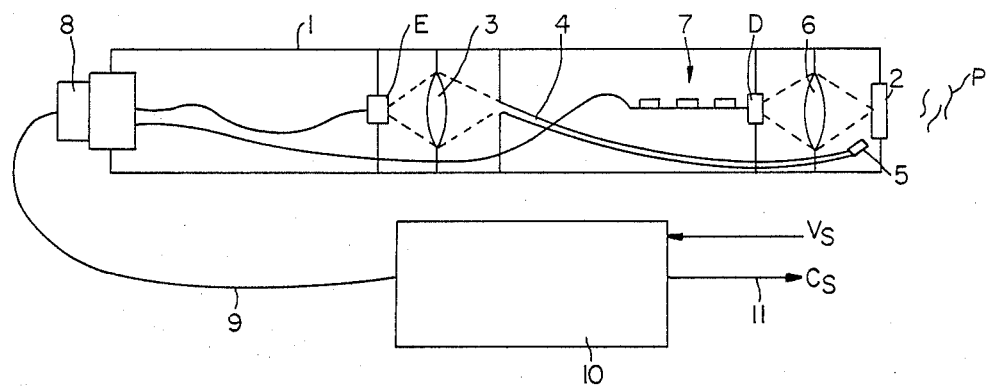

In the embodiment of FIG. 7, the optical components of an apparatus are fitted inside a protective tube 1 and the end of this protective tube is provided with a window 2, whereby the optical components in said protective tube are in contact with a composition to be measured for measuring the dry matter content of particles P contained in the composition. Inside the protective tube is fitted a radiation source E, the radiation emitted thereby being directed through a collimating lens 3 to an optical fibre 4, at whose end is a fiber-optical lens 5 for directing the radiation by way of window 2 into a composition to be measured for creating a zone to be radiated. The radiation reflected back from the radiated zone through window 2 is collected by means of a condenser lens 6 on a detector D, whereafter the radiation arriving in detector is preamplified at 7 and the amplified message is conveyed from protective tube 1 by way of an adapter 8 along a cable 9 into the electronics section 10 of the apparatus, which then supplies a consistency signal 11.

Figure 8:
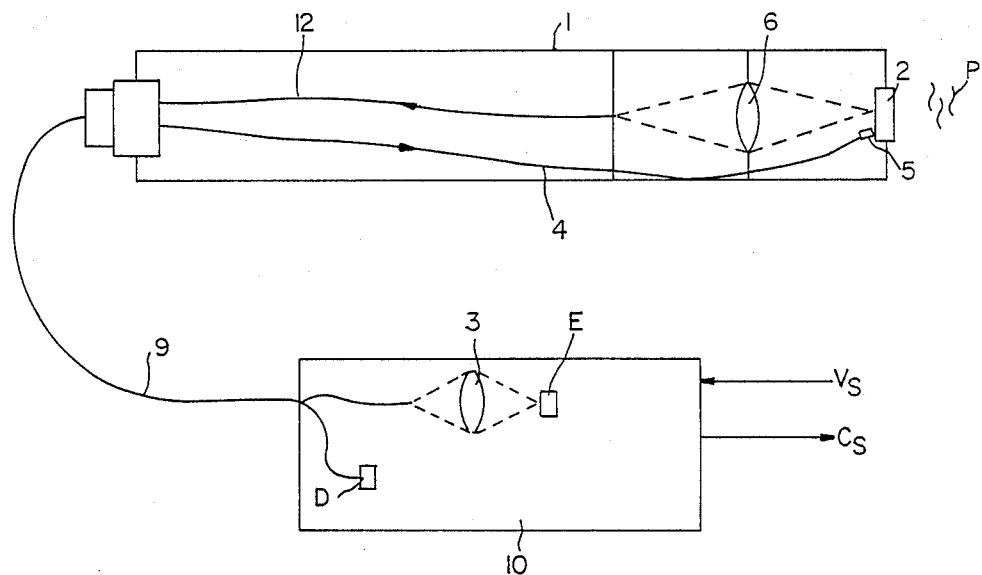

FIG. 8 is otherwise similar to FIG. 7 but a radiation source E and a collimating lens 3 as well as a detector D are mounted in a connection with the apparatus' electronics section, the electronics section and protective tube 1 being only connected by a bipolar fibre cable instead of a multicore cable shown in FIG. 7. Thus, the radiation issuing from a condenser lens 6 is delivered along an optical fibre 12 to the apparatus' electronics section 10. This embodiment serves to reduce the need for cables as compared to the embodiment of FIG. 7.

Figure 9:
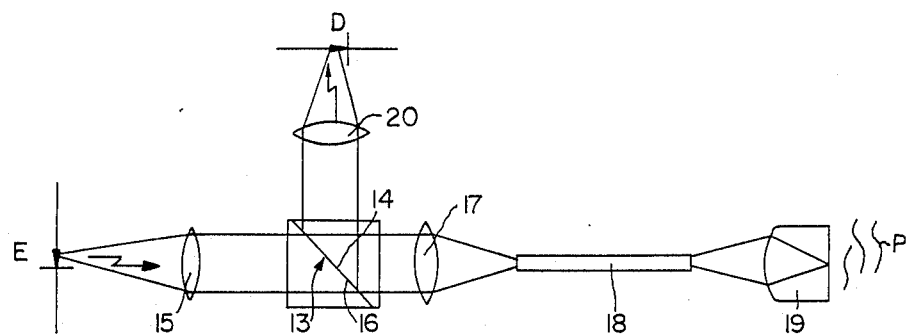

FIG. 9 illustrates an embodiment of the apparatus which employs a surface 16 that reflects at 14 and is permeable at 13 to radiation.

The radiation emitted from a radiation source E is directed through a lens 15 to a permeable surface 13, whereafter the light of a radiation source is further collected by means of a lens 17 on an optical fibre 18, at whose end the radiation is further directed by means of a lens 19 into a composition to be measured for producing a zone to be radiated. The radiation reflected back from a radiated zone finds its way in reverse order to a reflective surface 14 and further by way of a lens 20 to a detector D.

Figure 10:
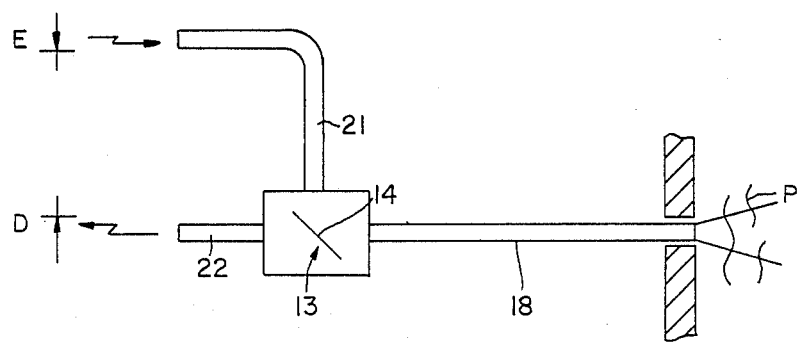

A system corresponding to that shown in FIG. 9 can also be embodied fiberoptically, as shown schematically in FIG. 10. Thus, in this case, a reflective and permeable surface 13 is directly used in conveying a radiation transmitted by optical fibres, without using any lens systems. A radiation directed from a radiation source E to an optical fibre 21 is reflected by way of a surface 14 to an optical fibre 18, whose end is fitted with a fiberoptical lens for allowing the radiation into a composition to be measured for producing a zone to be radiated. A radiation reflected back from this radiated zone is directed by way of optical fibre 18 through the reflective surface to a detector D along an optical fibre 22.

Figure 11:
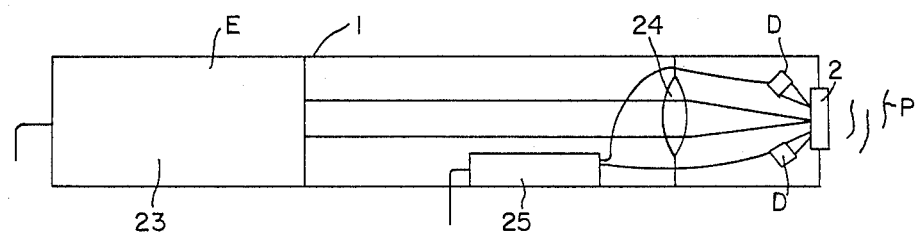

FIG. 11 shows an optical arrangement for the apparatus, designed by using laser technology. Inside a protective tube 1 is fitted a He-Ne laser device 23, from which a laser beam is directed through a focusing lens 24 and a window 2 into a composition. Inside protective tube 1, the frame of window 2 is provided with one or a plurality of detectors D, connected to the apparatus' electronics section 10. In FIG. 11, preamplifiers for the electronics section are fitted inside protective tube 1 in an element 25. The rest of the electronics are disposed outside the optical arrangement.

In view of the invention, the most essential part of the electronic circuit section 10 of an apparatus used in the method is shown in block diagrams in FIGS. 12 and 13. Its operation proceeds as follows:

A control voltage $V_{re}$ is used to stabilize the radiation from a radiation source E by utilizing a feedback from a photodiode S and a resistance $R_S$. The radiation source can also be non-stabilized. The radiation output must be over 2 mW.

From the radiation source, radiation is directed by way of the optical arrangements shown in FIGS 7–11 into a composition to be examined. A zone to be radiated fulfils the scale condition stated in the theoretical basis of the invention, considering the size of particles contained in a composition to be examined.

Referring to FIG. 12, the radiation that has reached detector D is converted into current and in a load resistance $R_D$ into voltage. This voltage signal is amplified by a preamplifier $A_0$ and its direct voltage component is eliminated by means of a filter $F_0$. The preamplifier sensitivity must exceed 5 kV/W. The lower limit frequency of filter $F_0$ is circa 100 Hz.

The maximum gain of amplifiers $A_{11}$ and $A_{12}$ must exceed 60 000 for a sufficient level of signal $u_0$. The gain of amplifier $A_{11}$ is controlled by means of an integrating level adjustment amplifier $A_{OAGC}$, having a time constant of circa 1 s, in a manner that the mean peak value of pulses $u_0$ and $u_2$ does not exceed a reference voltage $V_{r0}$ (circa 7 V). Peak values are measured by means of peak value detectors $u_{p0}$ and $u_{p2}$.

Detector $u_{p0}$ measures the positive peak value of $u_0$ and $u_{p2}$ measures the peak-to-peak value of $u_2$. Detector $u_{p1}$ measures the value of $u_1$ the same way as $u_{p2}$ measures the values of $u_2$. The value of a tracking time constant is circa 400 $\mu$s and the holding time constant circa 80 ms. Since the signal must be subjected to derivation, its noise bandwidth must be optimized for maintaining a sufficiently good signal-to-noise ratio. The signal-to-noise ratio remains sufficient when the passband of the filter $F_1$ is adjusted as a function of mass flow rate. Approximate data of the flow rate is obtained from voltage $u_V$ for controlling the band of filter $F_1$.

Voltage $u_V$ is produced by means of computational circuits $A_{20}$ and $A_{21}$ of FIG. 13 as well as by means of a summing amplifier $A_{22}$ (circuit $F_{c1}$ in FIG. 12) as a weighted sum of the ratios of voltages $u_{p0}$, $u_{p1}$ and $u_{p2}$. The weighting factor $K_{10}$ of ratio $u_{p1}/u_{p0}$ is circa 0.53 and the weighting factor $K_{21}$ of ratio $u_{p2}/u_{p1}$ is circa 0.72. Thus, when using value 10 V for voltage $V_r$, the scale of voltage $u_v$ will be 1 V for rate 1 m/s.

A suitable bandwidth is selected by means of comparators $A_{23}$, $A_{24}$, $A_{25}$, and $A_{26}$ controlled by voltage $u_v$ as well as by means of relays $R_0$, $R_1$, $R_2$ and $R_3$ by connecting the one of filters $B_0$, $B_1$, $B_2$, $B_3$ or $B_4$, which is most suitable for a particular rate range in question, between amplifiers $A_{11}$ and $A_{12}$. The voltage division provided by resistances $R_{v0}$, $R_{v1}$, $R_{v2}$, $R_{v3}$ and $R_{v4}$ determines the rates at which the change of bandwidth occurs.

Suitable filters are Bessel-type filters, of tenth order. Delays are approximately 21, 10, 6.8, 4.7 and 3.5 microseconds when change-over speeds are circa 0.6, 1.4, 2.75 and 4.25 m/s. The diameter of an illuminated zone is then 50 microns and derivation time constants $T_1$ and $T_2$ are 10–20 microseconds.

With the above time constants, derivation units $D_1$ and $D_2$ produce voltages $u_1$ and $u_2$ from voltage $u_0$. A positive threshold voltage required by a comparator $C_{2+}$ is obtained as a weighted sum of voltages $u_{p2}$ and $u_v$ from a summing circuit $A_{19}$, in which the weighting factors are roughly as follows: $K_2$ circa 0.37 and $K_v$ circa 0.25. The constant $V_B$ is circa 0.41 V. A negative threshold voltage is produced by an inverter I. Comparator $C_{2+}$ sets a flip-flop $FF_1$ when $u_2$ exceeds the positive threshold voltage, which happens at the final end of FIG. 4. The next overrun of threshold voltage on comparator $C_{2+}$ sets a flip-flop $FF_2$.

This is followed by going below a negative threshold voltage and that is detected by comparator $C_{2-}$, which resets flip-flops $FF_1$ and $FF_2$.

Comparators $C_0$ and $C_1$ prevent by way of NOR-gates the setting of flip-flop $FF_2$ as a result of noise and disturbancies. Comparator $C_0$ compares the gain adjustment voltage $U_{AGC}$ with a reference value $V_{rd}$ (circa 10 V) and prevents the operation of flip-flop $FF_2$, in case the signal is too low. Comparator $C_1$ prevents the resetting of flip-flop $FF_2$ as a result of noise.

Figure 6:
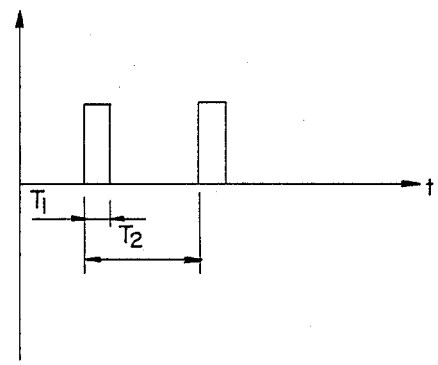

The output waveform of flip-flop $FF_2$ is as shown in FIG. 6 and, by means of a filter $F_{21}$ having a buffer amplifier, it is processed into the voltage $u_d$ of equation 16. The upper limit frequency of filter $F_{21}$ is below 1 Hz.

A computational circuit $A_{16}$ produces a voltage $u_{cs}$ by squaring voltage $u_d$, scaled by voltage $V_{rc}$. The thus obtained voltage $u_{cs}$ can be processed with prior known methods to form a desired consistency message.

In case a microprocessor is used, the consistency calculation can be effected by measuring the on-times of signals $T_1$ and $T_2$ by means of a timer circuit or a counter, which is either inside the microprocessors, included in a peripheral circuit or is an external circuit. The averages and a desired digital message are calculated from the obtained times $T_1$ and $T_2$ by way of a program.

Times $T_1$ and $T_2$ can also be determined by way of a program after recording in the memory of a microprocessor a sufficiently long sequence of samples of signal $u_0$ with a resolution of below 10 $\mu$s.

The obtained message can be transformed by means of a digital-analog converter into an analogous standard signal in a desired scale or it can be output by way of the digital interface of a microprocessor onto a control system.

The method and its theoretical basis are described above so that the diameter of a zone to be radiated exceeds the smallest dimension of particles. As an alternative, it is also possible to have such scaling that the diameter of a zone to be radiated is less than the smallest dimension of particles. In this case, the form of an intensity function changes to some degree, as a skilled person can readily appreciate, but the characteristics of the second derivative (singularities) of an intensity function are still discernible.

I claim:

1. A method for measuring the properties, especially the dry matter content of a composition consisting of a liquid and solid particles, said method comprising
   leading electromagnetic radiation into the composition,
   maintaining the size of a zone to be radiated substantially constant,
   setting the composition and the zone to be radiated in motion relative to each other,
   measuring with a measuring means the intensity of radiation reflecting or scattering back from an electromagnetically radiated zone, the signals therefrom being processed into messages proportional to the properties, especially the dry matter content of a composition, wherein
   the electromagnetic radiation led into a composition is given a wavelength that is smaller than the smallest dimension of the particles in a composition to be measured,
   an intensity function is formed as a result of the movement of an individual particle arriving in and passing by any given zone exposed to radiation and
   the intensity function is processed for finding out time relationships that are proportional to the thus appearing properties of a particle.

2. A method as set forth in claim 1, wherein an elliptical or circular area is used as a zone to be radiated.

3. A method as set forth in claim 1 wherein the greatest diameter of a zone to be radiated is selected to be smaller than the greatest dimension of particles to be measured from the composition but greater than the smallest dimension of particles to be measured in the composition.

4. A method as set forth in claim 1, wherein the composition is set in motion and the zone to be radiated is kept stationary.

5. A method as set forth in claim 1 wherein a time-dependent counter-function ($u_0$) of a function ($I_0 = f(D, \gamma_1, \gamma_2)$) corresponding to the surface area of particular figures in a zone to be radiated is derived two times relative to time for discovering the singularities of the second derivative of counter-function ($u_0$), an apparatus' electronics circuit is used to measure analogically and/or digitally, as individual particles travel past a zone to be radiated, a time interval ($T_1$) between two successive, opposite-sign singularities, and a repetition interval ($T_2$) such as the interval between the above pairs of singularities, which corresponds to a distance between successive particles as they travel past a zone to be radiated, an apparatus' electronics circuit is used to produce an electric message $u_{cs} = f(T_1, T_2)$, which is proportional to the consistency of a composition and whose general configuration is $u_{cs} = V_r(T_1/T_2)^2$, wherein $V_r$ is a reference voltage.

6. An apparatus for carrying out the method of claim 1, said apparatus comprising:
a radiation source,
means for leading the radiation of said radiation source into a composition to be measured for producing a zone to be radiated,
a detector,
means for directing the radiation reflecting or scattering back from a radiated zone onto said detector, and
a block comprising electronic circuits, which is connected to detector, wherein
said electronic circuits block comprises means for processing a time-dependent electric counter-function of the intensity of reflecting or back-scattering radiation for producing signals representing the configuration of particles contained in the composition and means for producing a message proportional to the properties, especially the dry matter content of the composition.

7. An apparatus as set forth in claim 6, wherein said electronics component comprises:
an amplifying and filtering unit,
two successive derivation units,
two flip-flops,
a threshold voltage producing unit,
comparators for controlling flip-flops according to the variations in voltages arriving by way of derivation units, and
a means for producing a message, which is formed on the basis of the output of flip-flop and which represents the dry matter content.

8. An apparatus as set forth in claim 6, wherein, in order to optimize the signal-to-noise ratio, the passband of a filter between amplifier units is adapted to be selected by means of a selector circuit, whose input variables comprise voltages, proportional to voltages acting upstream of derivation units, between and/or downstream of derivation units, and whose output comprises a voltage, which is produced on the basis of voltages preferably as a weighted sum thereof and on the basis of which a comparator circuit is operated to switch on the passband of filter.

9. A method as set forth in claim 2, wherein the greatest diameter of a zone to be radiated is selected to be smaller than the greatest dimension of particles to be measured from the composition but greater than the smallest dimension of particles to be measured in the composition.

10. A method as set forth in claim 2, wherein the composition is set in motion and the zone to be radiated is kept stationary.

11. A method as set forth in claim 3, wherein the composition is set in motion and the zone to be radiated is kept stationary.

12. A method as set forth in claim 2, wherein
a time-dependent counter-function ($u_0$) of a function ($I_0 = f(D, \gamma_1, \gamma_2)$) corresponding to the surface area of particle figures in a zone to be radiated is derived two times relative to time for discovering the singularities of the second derivative of counter-function ($u_0$), an apparatus' electronics circuit is used to measure analogically and/or digitally, as individual particles travel past a zone to be radiated, a time interval ($T_1$) between two successive, opposite-sign singularities, which corresponds to the diameter of particles, and a repetition interval ($T_2$) such as the interval between the above pairs of singularities, which corresponds to a distance between successive particles as they travel past a zone to be radiated, an apparatus' electronics circuit is used to produce an electric message $u_{cs} = f(T_1, T_2)$, which is proportional to the consistency of a composition and whose general configuration is $u_{cs} = V_r(T_1/T_2)^2$, wherein $V_r$ is a reference voltage.

13. A method as set forth in claim 3, wherein
a time-dependent counter-function ($u_0$) of a function ($I_0 = f(D, \gamma_1, \gamma_2)$) corresponding to the surface area of particle figures in a zone to be radiated is derived two times relative to time for discovering the singularities of the second derivative of counter-function ($u_0$), an apparatus' electronics circuit is used to measure analogically and/or digitally, as individual particles travel past a zone to be radiated, a time interval ($T_1$) between two successive, opposite-sign singularities, which corresponds to the diameter of particles, and a repetition interval ($T_2$) such as the interval between the above pairs of singularities, which corresponds to a distance between successive particles as they travel past a zone to be radiated, an apparatus' electronics circuit is used to produce an electric message $u_{cs} = f(T_1, T_2)$, which is proportional to the consistency of a composition and whose general configuration is $u_{cs} = V_r(T_1/T_2)^2$, wherein $V_r$ is a reference voltage.

14. A method as set forth in claim 4, wherein
a time-dependent counter-function ($u_0$) of a function ($I_0 = f(D, \gamma_1, \gamma_2)$) corresponding to the surface area of particle figures in a zone to be radiated is derived two times relative to time for discovering the singularities of the second derivative of counter-function ($u_0$), an apparatus' electronics circuit is used to measure analogically and/or digitally, as individual particles travel past a zone to be radiated, a time interval ($T_1$) between two successive, opposite-sign singularities, which corresponds to the diameter of particles, and a repetition interval ($T_2$) such as the interval between the above pairs of singularities, which corresponds to a distance between successive particles as they travel past a zone to be radiated, an apparatus' electronics circuit is used to produce an electric message $u_{cs} = f(T_1, T_2)$, which is proportional to the consistency of a composition and whose general configuration is $u_{cs}=V_r(T_1/T_2)^2$, wherein $V_r$ is a reference voltage.

15. An apparatus for carrying out the method of claim 2, said apparatus comprising:
a radiation source,
means for leading the radiation of said radiation source into a composition to be measured for producing a zone to be radiated,
a detector,
means for directing the radiation reflecting or scattering back from a radiated zone onto said detector, and
a block comprising electronic circuits, which is connected to detector, wherein
said electronic circuits block comprises means for processing a time-dependent electric counter-function of the intensity of reflecting or back-scattering radiation for producing signals representing the configuration of particles contained in the composition and means for producing a message proportional to the properties, especially the dry matter content of the composition.

16. An apparatus for carrying out the method of claim 3, said apparatus comprising:
a radiation source,
means for leading the radiation of said radiation source into a composition to be measured for producing a zone to be radiated,
a detector,
means for directing the radiation reflecting or scattering back from a radiated zone onto said detector, and
a block comprising electronic circuits, which is connected to detector, wherein
said electronic circuits block comprises means for processing a time-dependent electric counter-function of the intensity of reflecting or back-scattering radiation for producing signals representing the configuration of particles contained in the composition and means for producing a message proportional to the properties, especially the dry matter content of the composition.

17. An apparatus for carrying out the method of claim 4, said apparatus comprising:
a radiation source,
means for leading the radiation of said radiation source into a composition to be measured for producing a zone to be radiated,
a detector,
means for directing the radiation reflecting or scattering back from a radiated zone onto said detector, and
a block comprising electronic circuits, which is connected to detector, wherein
said electronic circuits block comprises means for processing a time-dependent electric counter-function of the intensity of reflecting or back-scattering radiation for producing signals representing the configuration of particles contained in the composition and means for producing a message proportional to the properties, especially the dry matter content of the composition.

18. An apparatus for carrying out the method of claim 5, said apparatus comprising:
a radiation source,
means for leading the radiation of said radiation source into a composition to be measured for producing a zone to be radiated,
a detector,
means for directing the radiation reflecting or scattering back from a radiated zone onto said detector, and
a block comprising electronic circuits, which is connected to detector, wherein
said electronic circuits block comprises means for processing a time-dependent electric counter-function of the intensity of reflecting or back-scattering radiation for producing signals representing the configuration of particles contained in the composition and means for producing a meassage proportional to the properties, especially the dry matter content of the composition.

* * * * *

UNITED STATES PATENT AND TRADEMARK OFFICE
CERTIFICATE OF CORRECTION

PATENT NO. : 4,791,305
DATED : December 13, 1988
INVENTOR(S) : Karaila

It is certified that error appears in the above—identified patent and that said Letters Patent is hereby corrected as shown below:

On the Title Page, change "[21] Appl. No.: 271,143" to --[21] Appl. No.: 114,368--.

Signed and Sealed this

Sixteenth Day of May, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,791,305

DATED : December 13, 1988

INVENTOR(S) : Ilkka Karaila

It is certified that error appears in the above-identified patent and that said Letters Patent is hereby corrected as shown below:

On the Title Page, change "[73] Assignee: Valmey Oy, Tampere, Finland" to --[73] Assignee: Valmet Oy, Tampere Finland--

Signed and Sealed this
Twelfth Day of December, 1989

Attest:

JEFFREY M. SAMUELS

*Attesting Officer*     *Acting Commissioner of Patents and Trademarks*